United States Patent [19]

Losell

[11] 4,214,779
[45] Jul. 29, 1980

[54] COUPLING DEVICE

[75] Inventor: Ingvar E. Losell, Staffanstorp, Sweden

[73] Assignee: Gambro AB, Sweden

[21] Appl. No.: 880,774

[22] Filed: Feb. 24, 1978

[30] Foreign Application Priority Data

Mar. 7, 1977 [SE] Sweden ............................. 7702496

[51] Int. Cl.² ............................................ F16L 35/00
[52] U.S. Cl. .................................... 285/93; 285/334.3; 285/319; 285/423; 285/DIG. 22; 128/214 R
[58] Field of Search .................. 285/93, 314, 334.2, 285/334.3, 423, DIG. 22, DIG. 11; 138/103; 128/214 R

[56] References Cited

U.S. PATENT DOCUMENTS

| | | | |
|---|---|---|---|
| 2,487,241 | 11/1949 | Hilton | 285/334.3 X |
| 3,158,380 | 11/1964 | Carrell et al. | 285/DIG. 11 |
| 3,447,570 | 1/1969 | Collins | 128/214 R X |
| 3,640,552 | 2/1972 | Demler | 285/DIG. 22 |
| 3,850,202 | 11/1974 | Morgan | 128/214 R X |
| 3,898,988 | 8/1975 | Morgan | 138/103 X |
| 3,990,445 | 11/1976 | Lundguist | 128/214 R |

FOREIGN PATENT DOCUMENTS

| | | | |
|---|---|---|---|
| 845563 | 6/1970 | Canada | 285/319 |
| 350822 | 10/1972 | Sweden | 285/319 |
| 7313489 | 12/1976 | Sweden | 285/93 |
| 1,169,507 | 11/69 | United Kingdom | |
| 1,355,897 | 6/74 | United Kingdom | |
| 1,443,136 | 7/76 | United Kingdom | |
| 1,480,904 | 7/77 | United Kingdom | |

*Primary Examiner*—Dave W. Arola
*Attorney, Agent, or Firm*—Lerner, David, Littenberg & Samuel

[57] ABSTRACT

A coupling device for joining together two fluid conduits and for providing fluid access to fluid in the fluid conduits. The device comprises a first coupling member which is adapted to be connected to one of the fluid conduits and a second coupling member adapted to be connected to the other fluid conduit. The first and second coupling members are adapted to be connected together to define an axial fluid passage therethrough between the two fluid conduits. An elastic member having an axial fluid opening therethrough is interposed between the first and second coupling members and the axial fluid opening thereof is axially aligned with the axial fluid passage defined by the first and second coupling members. Connecting means are also provided for connecting the first and second coupling members together to compress the elastic member between the first and second coupling members to seal the axial fluid passage. Also, at least one of the first and second coupling members includes an opening therethrough adjacent to the wall of the elastic member whereby selective fluid communication with the fluid in the fluid conduits can be obtained through the wall of the elastic member.

13 Claims, 4 Drawing Figures

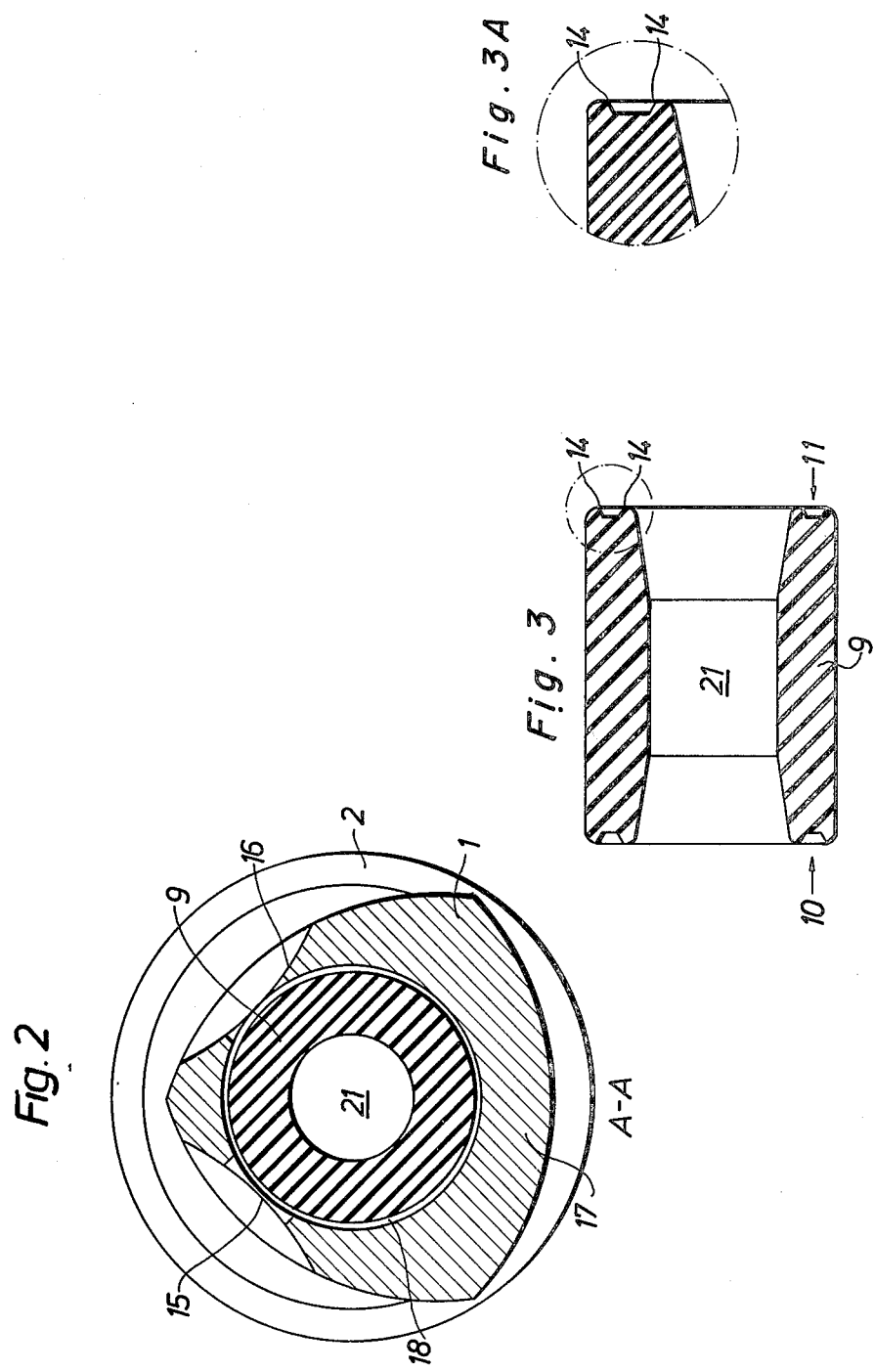

COUPLING DEVICE

BACKGROUND OF THE INVENTION

The present invention relates to coupling devices for joining together two fluid conduits and more particularly to such coupling devices which also provide access to the fluid in the fluid conduits. In the context of the present invention, the term fluid means gases as well as liquids.

Coupling devices for joining together of two fluid conduits are well known. Such devices are useful for a wide variety of purposes in which it is desirable to connect one conduit to another conduit to allow fluid to flow from one conduit into and through the other conduit. In most instances it also is desirable to make this connection so that there is no leakage or spillage at the junction of the two conduits. Thus, the coupling device serves not only to provide a fluid passage therethrough but to also provide a means for sealing such fluid passage. Such devices are particularly useful in joining together the fluid conduits for blood and dialysis liquid in dialysis systems where it is most important that there be no leakage between the connections.

Often times it is also desirable to provide means for taking of samples of the fluid passing in the fluid conduits and/or for injecting material into the fluid. For example, with blood and dialysis liquid conduits for dialysis systems, such samples and/or injections can be made with the help of cannulas or the like. In such cases, it is most desirable to take such samples or inject such materials without causing any leakage of the fluid from the fluid conduit.

SUMMARY OF THE INVENTION

The present invention provides a coupling device for joining together two fluid conduits while at the same time providing for fluid access to the fluid passing through the fluid conduits. The coupling device comprises a first coupling member which is adapted to be connected to one of the fluid conduits and a second coupling member adapted to be connected to the other fluid conduit. The first and second coupling members in turn are adapted to be connected so as to define an axial fluid passage therethrough between the two fluid conduits. An elastic member having an axial fluid opening therethrough is interposed between the first and second coupling members and has its axial opening axially aligned with the axial fluid passage defined by such first and second coupling members. Connecting means are provided for connecting the first and second coupling members together to axially compress the elastic member between the first and second coupling members in order to seal the fluid passage. At least one of the first and second coupling members includes an opening therethrough adjacent to the wall of the elastic member whereby selective fluid communication with the fluid in the fluid conduit can be obtained through the wall of the elastic member.

Accordingly, the coupling device of the present invention provides a simple reliable device which allows for the injection and/or withdrawal of samples through an elastic wall with the help of cannulas or the like without the risk of leakage.

In a preferred embodiment of the present invention, the elastic member is a tubular elastic member which is adapted to be compressed between axial end faces of the mating ends of the first and second coupling members. Additionally, either or both of the mating ends may be provided with an annular groove for guiding of the respective ends of the tubular elastic member.

In another preferred embodiment, either or both of the mating ends of the first and second coupling members are provided with conically projecting parts which are adapted to mate with complementary surfaces of the elastic tubular member so that the conically projecting parts of the mating ends are tightly pressed inwardly into the axial fluid opening through the elastic tubular member when the first and second coupling members are connected together by the connecting means.

In a still further preferred embodiment, the connecting means comprises a circumferential groove on the surface of the first coupling member and hook means on the second coupling member which is adapted to engage the circumferential groove so that the elastic member is axially compressed between the first and second coupling members.

In another embodiment of the present invention, the one coupling member having the opening therethrough adjacent the wall of the elastic member is provided with a rigid wall of relatively hard material on the opposite side of the axial fluid passage from the opening in order to prevent accidential penetration through such wall by means of the cannula used to inject and/or withdraw samples.

These and further features and characteristics of the present invention will be apparent from the following detailed description in which reference is made to the enclosed drawings which illustrate a preferred embodiment of the present invention.

BRIEF DESCRIPTION OF THE DRAWINGS

FIG. 2 is a cross-sectional view taken along lines A—A of FIG. 1;

FIG. 3 is an enlarged sectional view of the elastic member of the coupling device of the present invention in its disassembled unclamped position; and FIG. 3A is a still further enlarged sectional view of the portion of the elastic member within the circle portion of FIG. 3.

DESCRIPTION OF THE PREFERRED EMBODIMENT

Figure 1:
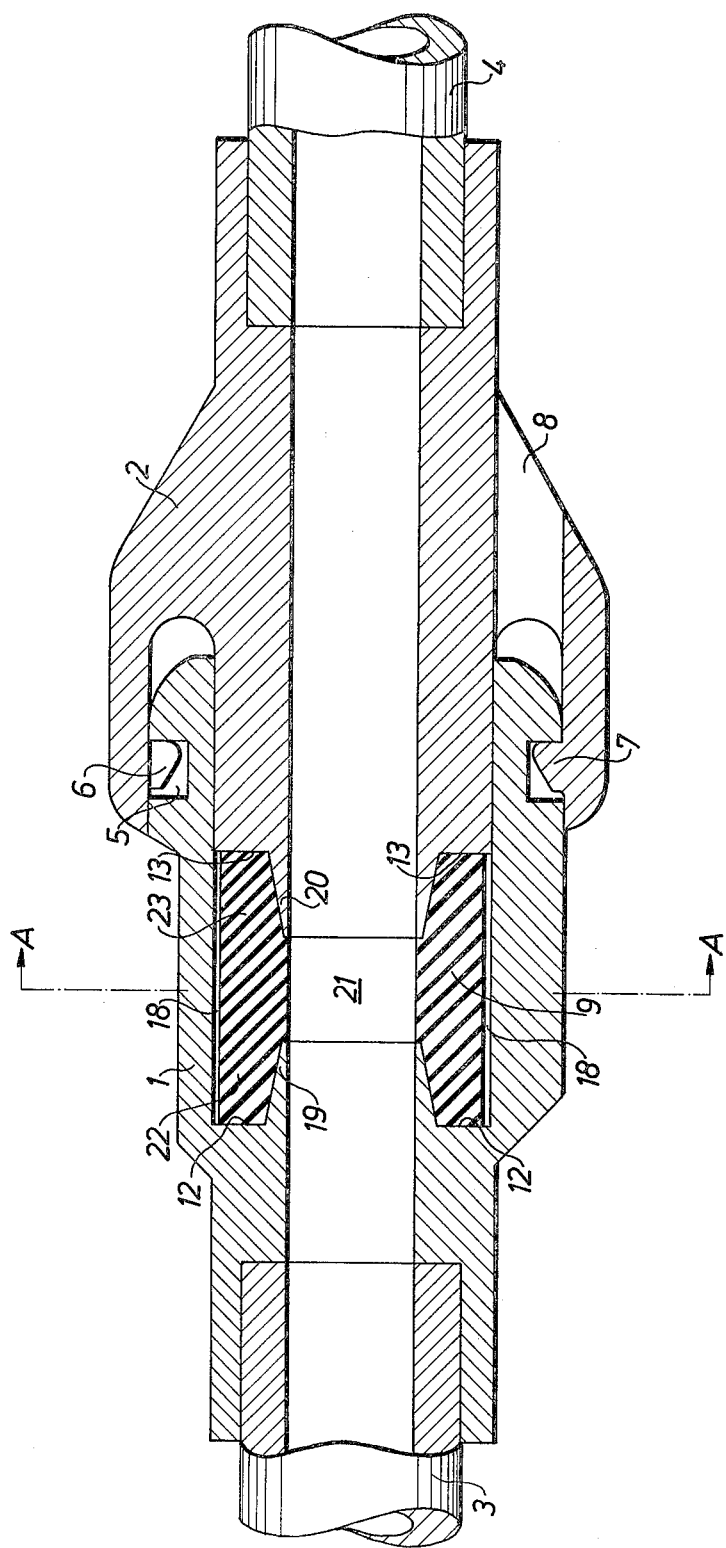
FIG. 1 is a sectional view of the coupling device according to the present invention.

As the coupling device of the present invention is mainly intended for being connected into conduits for blood and dialysis liquid in dialysis systems, the present invention will be described in such content. However, it should be realized that the device may also be used in other instances, for example in connection with oxygenerators and in fact, it can be used for coupling or joining together any two fluid conduits. In this regard, it should be noted that the term fluid is intended here to mean gases as well as liquids.

Turning first to FIG. 1, there is shown a longitudinal sectional view of the coupling device according to the present invention in which two axially mating coupling members 1 and 2 are shown connected to flexible tubes or other types of fluid conduits 3 and 4. In principle, however, there is nothing to prevent either of the components or members 1 and 2 from constituting a part of a housing to which a flexible tube may be connected. The construction in such a case will be substantially the same as if two flexible tubes are being joined together.

The axially mating component 1 is provided with a circumferential groove 5 which is engaged by hooks 6 and 7 on the axially mating component or member 2. The hooks 6 and 7 are arranged about the outside diameter of an annular groove formed in the end of component 2. It is into this annular groove that the portion of component 1 having the circumferential groove 5 therein is inserted so that the hooks 6 and 7 may snap into the groove 5. For reasons of manufacturing technique, these hooks 6 and 7 are arranged straight in front of through-hooks 8. This makes it possible for the component 2 to be manufactured by means of a simple two-part molding tool, as is well known in the art. In FIG. 1, only two hooks 6 and 7 are shown. However, in practice, preferably three or more such hooks are used. Of the two hooks shown, only the hook 7 is sectioned in order to indicate that only this hook is located in the sectional plane. The hook 6 on the other hand is peripherally displaced to a greater or lesser extent in relation to this section.

In FIGS. 3 and 3A, there is shown an elastic insert element 9 which is adapted to be clamped between the two axially mating components 1 and 2 to seal the fluid passage through the coupling device. In its clamped state, shown in FIG. 1, the axial end faces 10 and 11 of the element 9 are pressed tightly against the corresponding axial end faces 12 and 13 of the two components or members 1 and 2. In this way, leakage is prevented across the end faces 10, 12, and 11, 13 which are mated together. In a preferred embodiment, the elastic insert 9 is provided on its end faces 10, 11 with concentrically arranged sealing beads 14 which further serve to improve the seal when the elastic member 9 is clamped between the axial end faces 12 and 13. Alternatively, corresponding sealing beads can be arranged on the surfaces 12 and 13 of the two axially mating components 1, 2 and against which the axial end faces 10 and 11 of the tubular elastic element 9 rest.

The cross-section of the coupling component or member 1 is best seen in FIG. 2 which shows a section taken along lines A—A of FIG. 1. FIG. 2 also indicates that the coupling member 1 is provided with two openings 15 and 16 which are intended for injection and/or taking of samples, which may be done by means of cannulas, through the wall of the elastic tubular member 9. To prevent the coupling member 1 from being wholly penetrated by such cannulas, the coupling member 1 is provided with a thicker wall section 17 straight in front of the openings 15 and 16. This wall 17, like the rest of the coupling component 1, is manufactured of a relatively rigid hard material. Such relatively hard material straight in front of the openings further insures that the wall section 17 will not accidentially be penetrated by means of the cannula. This protection against penetration is desirable since such penetration could be very dangerous to the person performing the sample taking owing to the risk of infection with, for example, hepatitis. Similarly, if the opening for providing access to the fluid through the wall of the elastic member 9 is situated in the region of the second coupling member 2, such coupling member 2 could also be provided with a thick rigid wall opposite such opening intended for injection and/or sample taking.

For further protection against penetration, the coupling member or component 1 having the opening or openings for injection and/or sample taking is of a substantially triangular cross-section having three walls joined together. The outer surface of one of the walls 17 is located further away from the center of the flow opening through the coupling component 1 than the other outer surfaces of the other two walls which are each provided with the opening or openings 15, 16. In this way, the section of the outer walls directly opposite from the openings are relatively thick so as to prevent accidential penetration by a cannula.

It is to be noted that after any injection and/or sample taking, the area of injection will be pressed together automatically by the axial pressure exerted by the two coupling members 1 and 2. Thus, there will be no leakage of fluid out of the opening in the side wall of the elastic member 9. This axial compression of the elastic tubular member 9 is further insured by the fact that the elastic element 9 is arranged with a play 18 within the coupling component or member 1, thereby insuring that the full axial compression force exerted between the coupling members 1 and 2 will act on the axial end faces 10, 11 of the elastic member 9.

On their axial end faces directed towards one another, the coupling members or components 1 and 2 are provided with conically projecting parts 19 and 20 which are matched to complementary surfaces of the tubular elastic member 9. In this way, the conically projecting parts 19 and 20 are adapted so that on snapping together of the two coupling members 1 and 2, the conically projecting parts 19 and 20 are tightly pressed into the axial hole 21 in the tubular elastic member 9 for further improvement of the seal. That is, the side walls of the elastic tubular member 9 engaging the conical parts 19 and 20 serve as a further seal in addition to the seal provided by mating of the axial end faces of the tubular elastic member 9 with the corresponding end surfaces of the coupling members 1 and 2.

Between the outer wall of the component 1 and the conically projecting part 19 there is provided an annular groove 22, the base of which constitutes the axial end surface 12 of the component 1. A corresponding but incompletely formed groove 23 is provided in the component or member 2. This groove 23 has a base 13 and is partly delimited by the conically projecting part 20. These grooves 22 and 23 serve to facilitate the assembly of the elastic tubular member 9 while at the same time the elastic tubular member is securely guided and locked in the desired position.

Naturally, the present invention is not limited simply to the above mentioned embodiment, but can be varied within the scope of the following patent claims. Different materials may be used, for example, for the different parts. It has been found suitable to use latex, silicone rubber, or polyurethane for the tubular elastic member 9. Other materials, however, may be used. Similarly, different thermoplastics such as PVC or polyethylene may be used for the coupling components 1 and 2. However, other thermoplastics, and also thermosetting resins, may also be used. For the rest, the different parts of the construction may be varied in shape without thereby exceeding the scope of the present invention.

What is claimed is:

1. A coupling device for joining together two fluid conduits and for providing fluid access to the fluid in the fluid conduits, said coupling device comprising:
    a first coupling member adapted to be connected to one of said fluid conduits;
    a second coupling member adapted to be connected to the other of said fluid conduits, said first and second coupling members being adapted to be connected together to define an axial fluid passage through said first and second coupling members between said two fluid conduits;

an elastic member having an axial fluid opening therethrough interposed between said first and second coupling members, said axial fluid opening of said elastic member being axially aligned with said axial fluid passage defined by said first and second coupling members;

connecting means for connecting said first and second coupling members together to axially compress said elastic member between said first and second coupling members to seal said axial fluid passage without compressing said elastic member transversely of the axial direction; at least one of said first and second coupling members including an overlapping wall section overlappping said elastic member, and an opening defined in said overlapping wall section to provide access to said elastic member; into engagement with said overlapping wall section and in line with the opening in said overlapping wall section and at least a portion of the wall of said elastic member in line with the opening in said overlapping wall section, being resealably penetrable to provide selective fluid communication with the fluid in said fluid conduits through said portion of the wall of said elastic member.

2. The coupling device of claim 1 wherein said first and second coupling members each have a mating end having an axial opening therein and having axial end surfaces, said first and second mating ends being axially connectable together by said connecting means with said axial end surfaces being directed toward one another and said axial openings thereof defining said axial fluid passage, and wherein said elastic member is axially compressed between said axial end surfaces.

3. The coupling device of claim 2 wherein said elastic member comprises a tubular elastic element having axial end surfaces adapted to mate with said axial end surfaces of said first and second coupling members.

4. The coupling device of claim 3 wherein said mating end of said first coupling member is provided with an annular groove in the end thereof for guiding one end of said tubular elastic element, said axial end surface of said first coupling member being defined by the bottom of said annular groove in said first coupling member.

5. The coupling device of claim 4 wherein said mating end of said second coupling member is also provided with an annular groove in the end thereof for guiding the other end of said tubular elastic element, said axial end surface of said second coupling member being defined by the bottom of said annular groove in said second coupling member.

6. The coupling device of claim 3 wherein said mating end of said first coupling member is provided with a conically projecting part and wherein a portion of said tubular elastic element is provided with a complementary surface adapted to mate with said conically projecting part whereby when said first and second coupling members are connected together by said connecting means, said conically projecting part is tightly pressed inwardly into said axial fluid opening through said tubular elastic element to further seal said fluid passage.

7. The coupling device of claim 6 wherein said mating end of said second coupling member is also provided with a conically projecting part and wherein a portion of said tubular elastic element is provided with a complementary surface adapted to mate with said conically projecting part whereby when said first and second coupling members are connected together by said connecting means, said conically projecting parts are tightly pressed inwardly into said axial fluid opening through said tubular elastic element to further seal said fluid passage.

8. The coupling device of claim 3 wherein each of said axial end surfaces of said tubular elastic element include at least one annular sealing bead thereon, said annular sealing beads being adapted to engage the axial end surfaces of said coupling members to seal said fluid passage.

9. The coupling device of claim 8 wherein each of said axial end surfaces of said tubular elastic element is provided with two concentrically arranged annular sealing beads.

10. The coupling device of claim 3 wherein said one coupling member having said overlapping wall section and said opening therein has three joined wall sections at the axial location of said opening surrounding said tubular elastic member, the outer surface of one of said wall sections being located a greater distance from the center of said axial opening in the mating end thereof than the outer surfaces of the other two wall sections.

11. The coupling device of claim 1 wherein said one coupling member having said overlapping wall section and said opening therein is further provided with a rigid wall section of relatively hard material on the opposite side of said axial fluid passage from said opening in said one coupling member to prevent access to the fluid in said fluid conduits through said opposite side of said axial fluid passage.

12. The coupling device of claim 1 wherein said connecting means comprises a circumferential groove on the surface of said first coupling member and hook means on said second member adapted to engage portions of said circumferential groove on said first coupling member to lock said first and second coupling member together to axially compress said elastic member between said first and second coupling members.

13. The coupling device of claim 12 wherein said circumferential groove is formed on the outer surface of a portion of said mating end of said first coupling member and wherein said second coupling member is provided with an annular groove in said mating end thereof which is adapted to receive said portion of said mating end of said first coupling member having said circumferential groove, and said hook means is formed in the outer side walls of said annular groove of said second coupling member so that said hook means engages portions of said circumferential groove when said mating end of said first coupling member is inserted into said annular groove of said second coupling member to axially compress said elastic member.

* * * * *

UNITED STATES PATENT AND TRADEMARK OFFICE
CERTIFICATE OF CORRECTION

PATENT NO. : 4,214,779

DATED : July 29, 1980

INVENTOR(S) : Ingvar E. Losell

It is certified that error appears in the above-identified patent and that said Letters Patent are hereby corrected as shown below:

laim 1 should read:

1. A coupling device for joining together two luid conduits and for providing fluid access to the fluid n the fluid conduits, said coupling device comprising:

a first coupling member adapted to be connected o one of said fluid conduits;

a second coupling member adapted to be connected o the other of said fluid conduits, said first and second oupling members being adapted to be connected together to efine an axial fluid passage through said first and second oupling members between said two fluid conduits;

an elastic member having an axial fluid opening herethrough interposed between said first and second coupling embers, said axial fluid opening of said elastic member eing axially aligned with said axial fluid passage defined y said first and second coupling members;

UNITED STATES PATENT AND TRADEMARK OFFICE
CERTIFICATE OF CORRECTION

PATENT NO. : 4,214,779

DATED : July 29, 1980

INVENTOR(S) : Ingvar E. Losell

It is certified that error appears in the above-identified patent and that said Letters Patent are hereby corrected as shown below:

at least one of said first and second coupling members including an overlapping wall section overlapping said elastic member, and an opening defined in said overlapping wall section to provide access to said elastic member;

connecting means for connecting said first and second coupling members together to axially compress said elastic member between said first and second coupling members to seal said axial fluid passage without compressing said elastic member transversely of the axial direction into engagement with said overlapping wall section; and at least a portion of the wall of said elastic member in line with the opening in said overlapping wall section being resealably penetrable to provide selective fluid communication with the fluid in said fluid conduits through said portion of the wall of said elastic member.

Signed and Sealed this

Twenty-eighth Day of October 1980

[SEAL]

Attest:

SIDNEY A. DIAMOND

Attesting Officer

Commissioner of Patents and Trademar